United States Patent
Shan

(10) Patent No.: US 10,225,800 B2
(45) Date of Patent: *Mar. 5, 2019

(54) PORTABLE DEVICE CONTROL METHOD AND DEVICE

(71) Applicant: Huawei Technologies Co., Ltd., Shenzhen (CN)

(72) Inventor: Zhenwei Shan, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,168

(22) Filed: Jan. 3, 2018

(65) Prior Publication Data
US 2018/0132181 A1    May 10, 2018

Related U.S. Application Data

(63) Continuation of application No. 15/326,305, filed as application No. PCT/CN2014/083451 on Jul. 31, 2014, now Pat. No. 9,894,611.

(51) Int. Cl.
*H04B 7/00* (2006.01)
*H04W 52/02* (2009.01)
(Continued)

(52) U.S. Cl.
CPC ...... *H04W 52/0229* (2013.01); *G06F 9/4856* (2013.01); *G06F 9/54* (2013.01);
(Continued)

(58) Field of Classification Search
CPC ........... H04W 52/0229; H04M 1/7253; H04M 2017/2531
(Continued)

(56) References Cited

U.S. PATENT DOCUMENTS 8,854,925 B1   10/2014   Lee et al.
9,572,232 B2   2/2017   Hack et al.
(Continued)

FOREIGN PATENT DOCUMENTS

CN   103108032 A   5/2013
CN   103442129 A   12/2013
(Continued)

OTHER PUBLICATIONS

Interactive method and system between intelligent watch and mobile terminal, Publication date Dec 11, 2013, machine translated from publication No. CN103442129A in PDF format, pp. 1-6.*
(Continued)

*Primary Examiner* — Sonny Trinh
(74) *Attorney, Agent, or Firm* — Conley Rose, P.C.

(57) ABSTRACT

A portable device control method and a device are described herein. The method includes establishing, by a first device using a wireless communications technology, a connection to a second device when the first device discovers the second device; determining, by the first device, a user is in a first scene mode, wherein the first scene mode is a motion status, a health detection status or a sleep status; determining, by the first device based on a preset execution policy, an execution device of a first application; and sending, by the first device to the second device, an instruction message for executing the first application when the execution device is the second device.

17 Claims, 11 Drawing Sheets

(51) Int. Cl.
*G06F 19/00* (2018.01)
*G06F 9/48* (2006.01)
*G06F 9/54* (2006.01)
*H04L 29/08* (2006.01)
*H04W 76/14* (2018.01)
*H04W 76/20* (2018.01)

(52) U.S. Cl.
CPC .......... *G06F 19/00* (2013.01); *G06F 19/3418* (2013.01); *G06F 19/3481* (2013.01); *H04L 67/22* (2013.01); *H04W 76/14* (2018.02); *H04W 76/20* (2018.02); *Y02D 70/1262* (2018.01); *Y02D 70/142* (2018.01); *Y02D 70/144* (2018.01); *Y02D 70/162* (2018.01); *Y02D 70/166* (2018.01); *Y02D 70/26* (2018.01)

(58) Field of Classification Search
USPC .................................. 455/41.2, 420, 88, 230
See application file for complete search history.

(56) References Cited

U.S. PATENT DOCUMENTS

| | | | |
|---|---|---|---|
| 9,692,839 B2* | 6/2017 | Davis | ............... H04L 67/22 |
| 2010/0272258 A1 | 10/2010 | Sadovsky et al. | |
| 2011/0231469 A1 | 9/2011 | Wolman et al. | |
| 2012/0072481 A1 | 3/2012 | Nandlall et al. | |
| 2013/0237147 A1 | 9/2013 | Dearman | |
| 2014/0313867 A1 | 10/2014 | Lee et al. | |
| 2016/0036953 A1 | 2/2016 | Lee et al. | |
| 2016/0367157 A1* | 12/2016 | Blake | ............... A61B 5/02405 |
| 2017/0064063 A1 | 3/2017 | Watanabe | |

FOREIGN PATENT DOCUMENTS

| | | | |
|---|---|---|---|
| CN | 103823393 A | 5/2014 | |
| CN | 103902202 A | 7/2014 | |
| EP | 2456169 A1 | 5/2012 | |

OTHER PUBLICATIONS

Machine Translation and Abstract of Chinese Publication No. CN103108032, dated May 15, 2013, 22 pages.
Machine Translation and Abstract of Chinese Publication No. CN103442129, dated Dec. 11, 2013, 15 pages.
Machine Translation and Abstract of Chinese Publication No. CN103442129, dated Dec. 11, 2013, 4 pages.
Machine Translation and Abstract of Chinese Publication No. CN103823393, dated May 28, 2014, 16 pages.
Machine Translation and Abstract of Chinese Publication No. CN103902202, dated Jul. 2, 2014, 24 pages.
Messer A., et al., "Towards a Distributed Platform for Resource-Constrained Devices," XP010595515, IEEE computer Society, Jul. 2, 2002, 9 pages.
Yang, K., et al., "On Effective Offloading Services for Resource-Constrained Mobile Devices Running Heavier Mobile Internet Applications," XP011224535, IEEE Communication Magazine, vol. 46, No. 1, Jan. 2, 2008, 8 pages.
Foreign Communication From a Counterpart Application, European Application No. 14898583.1, Extended European Search Report dated Jun. 16, 2017, 12 pages.
Foreign Communication From a Counterpart Application, PCT Application No. PCT/CN2014/083451, English Translation of International Search Report dated Feb. 27, 2015, 2 pages.
Foreign Communication From a Counterpart Application, PCT Application No. PCT/CN2014/083451, English Translation of Written Opinion dated Feb. 27, 2015, 7 pages.

* cited by examiner

PORTABLE DEVICE CONTROL METHOD AND DEVICE

CROSS-REFERENCE TO RELATED APPLICATIONS

This application is a continuation of U.S. patent application Ser. No. 15/326,305, filed on Jan. 13, 2017, which is a National Stage of International Application No. PCT/CN2014/083451, filed on Jul. 31, 2014, all of which are hereby incorporated by reference in their entireties.

TECHNICAL FIELD

The present disclosure relates to the field of communications technologies, and in particular, to a portable device control method and a device.

BACKGROUND

Currently, applications supported by wearable smart devices (such as a smart band, a smart anklet, and smart glasses) tend to homogeneity. For example, many wearable smart devices support a step counting application, a location application, a heart rate detection application, and the like.

Generally, all wearable smart devices automatically execute an application corresponding to a scene mode. Specifically, when a user is in a specific scene mode, all wearable smart devices that are carried by the user and can execute an application corresponding to the scene mode execute the application. For example, when the user is in a motion scene mode, all wearable smart devices that are carried by the user and can execute the step counting application automatically execute the step counting application.

In the foregoing solution, because multiple wearable smart devices all execute an application corresponding to a same scene mode, total power consumed in a process of executing the application is relatively large.

SUMMARY

Embodiments of the present disclosure provide a portable device control method and a device, so as to reduce total power consumed in a process of executing a specific application.

According to a first aspect, a portable device control method is provided, where the method includes establishing, by a first device by using a wireless communications technology, a connection to a second device when the first device discovers the second device, where the first device is a device that controls a specific application of the second device; determining, by the first device, that a user is in a first scene mode; determining, by the first device according to a preset execution policy of a first application corresponding to the first scene mode, an execution device of the first application corresponding to the first scene mode, where the first application is any specific application corresponding to the first scene mode; and if the execution device is the second device, sending, by the first device, an instruction message for executing the first application to the second device, so that the second device executes the first application.

With reference to the first aspect, in a first possible implementation manner, the method further includes executing, by the first device, the first application if the execution device is the first device.

With reference to the first aspect, in a second possible implementation manner, after the determining an execution device of the first application corresponding to the first scene mode, the method further includes determining, by the first device according to a preset presentation policy, a presentation device for an execution result of the first application; and after the sending, by the first device, an instruction message for executing the first application to the second device, the method further includes if the presentation device is the first device, obtaining, by the first device, the execution result from the second device, and presenting, by the first device, the execution result; or if the presentation device is the second device, sending, by the first device, a presentation instruction message to the second device, so that the second device presents the execution result; or if the presentation device is a third device, obtaining, by the first device, the execution result from the second device, and sending a presentation instruction message to the third device, where the presentation instruction message carries the execution result and is used to instruct the third device to present the execution result, and the third device is a device, except the second device, that is discovered by the first device and to which the first device establishes a connection; or if the presentation device is a third device, sending, by the first device, a sending instruction message to the second device, and sending a presentation instruction message to the third device, where the sending instruction message is used to instruct the second device to send the execution result to the third device, the presentation instruction message is used to instruct the third device to present the execution result, and the third device is a device, except the second device, that is discovered by the first device and to which the first device establishes a connection.

With reference to the first possible implementation manner of the first aspect, in a third possible implementation manner, after the determining an execution device of the first application corresponding to the first scene mode, the method further includes determining, by the first device according to a preset presentation policy, a presentation device for an execution result of the first application; and after the executing, by the first device, the first application, the method further includes presenting, by the first device, the execution result if the presentation device is the first device; or if the presentation device is the second device, sending, by the first device, a presentation instruction message to the second device, where the presentation instruction message carries the execution result, so that the second device presents the execution result; or if the presentation device is a third device, sending, by the first device, a presentation instruction message to the third device, where the presentation instruction message carries the execution result and is used to instruct the third device to present the execution result, and the third device is a device, except the second device, that is discovered by the first device and to which the first device establishes a connection.

With reference to any one of the first aspect, or the first possible implementation manner to the third possible implementation manner of the first aspect, in a fourth possible implementation manner, after the executing the first application, the method further includes determining, by the first device, that the user is in a second scene mode, where the second scene mode is a scene mode in which execution of the first application is stopped; and if the execution device is the second device, sending, by the first device, an instruction message for stopping the execution of the first application to the second device, so that the second device stops the execution of the first application.

With reference to any one of the first aspect, or the first possible implementation manner to the fourth possible implementation manner of the first aspect, in a fifth possible implementation manner, before the determining, by the first device, that a user is in a first scene mode, the method further includes obtaining, by the first device, information about a specific application that can be executed by the second device; and the determining, by the first device according to a preset execution policy corresponding to the first scene mode, an execution device of the first application corresponding to the first scene mode includes determining, by the first device according to the preset execution policy corresponding to the first scene mode and information about a specific application that can be executed by the first device and the second device, the execution device of the first application corresponding to the first scene mode.

According to a second aspect, a portable device control method is provided, where the method includes establishing, by a second device by using a wireless communications technology, a connection to a first device when the second device is discovered by the first device, where the first device is a device that controls a specific application of the second device; when the first device determines that a user is in a first scene mode, and determines that the second device is an execution device of a first application corresponding to the first scene mode, receiving, by the second device, an instruction message sent by the first device and for executing the first application, where the first application is any specific application corresponding to the first scene mode; and executing, by the second device, the first application.

With reference to the second aspect, in a first possible implementation manner, after the executing the first application, the method further includes if the execution device is the first device and the presentation device is the second device, receiving, by the second device, a presentation instruction message sent by the first device, where the presentation instruction message carries the execution result; and presenting, by the second device, the execution result; or if the execution device is the second device and the presentation device is the first device, sending, by the second device, the execution result to the first device; or if the second device serves as both the execution device and the presentation device, receiving, by the second device, a presentation instruction message sent by the first device, and presenting, by the second device, the execution result; or if the execution device is the second device and the presentation device is a third device, sending, by the second device, the execution result to the first device, so that the first device sends a presentation instruction message to the third device, where the presentation instruction message carries the execution result and instructs the third device to present the execution result, and the third device is a device, except the second device, that is discovered by the first device and to which the first device establishes a connection; or if the execution device is the second device and the presentation device is a third device, receiving, by the second device, a sending instruction message sent by the first device, where the sending instruction message is used to instruct the second device to send the execution result to the third device; and sending, by the second device, the execution result to the third device, so that the third device presents the execution result, where the third device is a device, except the second device, that is discovered by the first device and to which the first device establishes a connection.

With reference to the second aspect or the first possible implementation manner of the second aspect, in a second possible implementation manner, after the executing, by the second device, the first application, the method further includes determining, by the first device, that the user is in a second scene mode; if the second device is the execution device of the first application, receiving, by the second device, an instruction message sent by the first device and for stopping execution of the first application, where the second scene mode is a scene mode in which the execution of the first application is stopped; and stopping, by the second device, the execution of the first application.

According to a third aspect, a first device is provided, including a discovery unit configured to discover a second device, where the first device is a device that controls a specific application of the second device; a connection unit configured to establish a connection to the second device by using a wireless communications technology; a determining unit configured to determine that a user is in a first scene mode, and determine, according to a preset execution policy of a first application corresponding to the first scene mode, an execution device of the first application corresponding to the first scene mode, where the first application is any specific application corresponding to the first scene mode; and a sending unit configured to, if the execution device is the second device, send an instruction message for executing the first application to the second device, so that the second device executes the first application.

With reference to the third aspect, in a first possible implementation manner, the first device further includes an execution unit configured to execute the first application if the execution device is the first device.

With reference to the third aspect, in a second possible implementation manner, the determining unit is further configured to determine, according to a preset presentation policy, a presentation device for an execution result of the first application; and if the presentation device is the first device, the first device further includes an obtaining unit configured to obtain the execution result from the second device, and a presentation unit configured to present the execution result; or if the presentation device is the second device, the sending unit is further configured to send a presentation instruction message to the second device, so that the second device presents the execution result; or if the presentation device is a third device, the first device further includes an obtaining unit configured to obtain the execution result from the second device, and the sending unit is further configured to send a presentation instruction message to the third device, where the presentation instruction message carries the execution result and is used to instruct the third device to present the execution result, and the third device is a device, except the second device, that is discovered by the first device and to which the first device establishes a connection; or if the presentation device is a third device, the sending unit is further configured to send a sending instruction message to the second device, and send a presentation instruction message to the third device, where the sending instruction message is used to instruct the second device to send the execution result to the third device, the presentation instruction message is used to instruct the third device to present the execution result, and the third device is a device, except the second device, that is discovered by the first device and to which the first device establishes a connection.

With reference to the first possible implementation manner of the third aspect, in a third possible implementation manner, the determining unit is further configured to determine, according to a preset presentation policy, a presentation device for an execution result of the first application; and if the presentation device is the first device, the first device further includes a presentation unit configured to present the execution result; or if the presentation device is the second device, the sending unit is further configured to send a presentation instruction message to the second device, where the presentation instruction message carries the execution result, so that the second device presents the execution result; or if the presentation device is a third device, the sending unit is further configured to send a presentation instruction message to the third device, where the presentation instruction message carries the execution result and is used to instruct the third device to present the execution result, and the third device is a device, except the second device, that is discovered by the first device and to which the first device establishes a connection.

With reference to any one of the third aspect, or the first possible implementation manner to the third possible implementation manner of the third aspect, in a fourth possible implementation manner, the determining unit is further configured to determine that the user is in a second scene mode, where the second scene mode is a scene mode in which execution of the first application corresponding to the first scene mode is stopped; and if the execution device is the second device, the sending unit is further configured to send an instruction message for stopping the execution of the first application to the second device, so that the second device stops the execution of the first application.

With reference to any one of the third aspect, or the first possible implementation manner to the fourth possible implementation manner of the third aspect, in a fifth possible implementation manner, the first device further includes an obtaining unit, where the obtaining unit is configured to obtain information about a specific application that can be executed by the second device; and the determining unit is configured to determine, according to the preset execution policy corresponding to the first scene mode and information about a specific application that can be executed by the first device and the second device, the execution device of the first application corresponding to the first scene mode.

According to a fourth aspect, a second device is provided, including a discovery unit configured to be discovered by a first device, where the first device is a device that controls a specific application of the second device; a connection unit configured to establish a connection to the first device by using a wireless communications technology; a receiving unit configured to receive an instruction message sent by the first device and for executing a first application, where the first application is any specific application corresponding to a first scene mode; and an execution unit configured to execute the first application.

With reference to the fourth aspect, in a first possible implementation manner, if the execution device is the first device and the presentation device is the second device, the receiving unit is further configured to receive a presentation instruction message sent by the first device, where the presentation instruction message carries the execution result; and the second device further includes a presentation unit configured to present the execution result; or if the execution device is the second device and the presentation device is the first device, the second device further includes a sending unit configured to send the execution result to the first device; or if the second device serves as both the execution device and the presentation device, the receiving unit is further configured to receive a presentation instruction message sent by the first device; and the second device further includes a presentation unit configured to present the execution result; or if the execution device is the second device and the presentation device is a third device, the second device further includes a sending unit configured to send the execution result to the first device, so that the first device sends a presentation instruction message to the third device, where the presentation instruction message carries the execution result and is used to instruct the third device to present the execution result, and the third device is a device, except the second device, that is discovered by the first device and to which the first device establishes a connection; or if the execution device is the second device and the presentation device is a third device, the receiving unit is further configured to receive a sending instruction message sent by the first device, where the sending instruction message is used to instruct the second device to send the execution result to the third device; and the second device further includes a sending unit configured to send the execution result to the third device, so that the third device presents the execution result, where the third device is a device, except the second device, that is discovered by the first device and to which the first device establishes a connection.

With reference to the fourth aspect or the first possible implementation manner of the fourth aspect, in a second possible implementation manner, the receiving unit is further configured to receive an instruction message sent by the first device and for stopping execution of the first application; and the execution unit is further configured to stop the execution of the first application.

According to a fifth aspect, a first device is provided, including a communications module configured to discover a second device and establish a connection to the second device by using a wireless communications technology, where the first device is a device that controls a specific application of the second device; a processor configured to determine that a user is in a first scene mode, and determine, according to a preset execution policy of a first application corresponding to the first scene mode, an execution device of the first application corresponding to the first scene mode, where the first application is any specific application corresponding to the first scene mode; and a transmitter configured to, if the execution device is the second device, send an instruction message for executing the first application to the second device, so that the second device executes the first application.

With reference to the fifth aspect, in a first possible implementation manner, the processor is further configured to execute the first application if the execution device is the first device.

With reference to the fifth aspect, in a second possible implementation manner, the processor is further configured to determine, according to a preset presentation policy, a presentation device for an execution result of the first application; and if the presentation device is the first device, the processor is further configured to obtain the execution result from the second device, and the first device further includes an output device configured to present the execution result; or if the presentation device is the second device, the transmitter is further configured to send a presentation instruction message to the second device, so that the second device presents the execution result; or if the presentation device is a third device, the processor is further configured to obtain the execution result from the second device, and the transmitter is further configured to send a presentation instruction message to the third device, where the presentation instruction message carries the execution result and is used to instruct the third device to present the execution result, and the third device is a device, except the second device, that is discovered by the first device and to which the first device establishes a connection; or if the presentation device is a third device, the transmitter is further configured to send a sending instruction message to the second device, and send a presentation instruction message to the third device, where the sending instruction message is used to instruct the second device to send the execution result to the third device, the presentation instruction message is used to instruct the third device to present the execution result, and the third device is a device, except the second device, that is discovered by the first device and to which the first device establishes a connection.

With reference to the first possible implementation manner of the fifth aspect, in a third possible implementation manner, the processor is further configured to determine, according to a preset presentation policy, a presentation device for an execution result of the first application; and if the presentation device is the first device, the first device further includes an output device configured to present the execution result; or if the presentation device is the second device, the transmitter is further configured to send a presentation instruction message to the second device, where the presentation instruction message carries the execution result, so that the second device presents the execution result; or if the presentation device is a third device, the transmitter is further configured to send a presentation instruction message to the third device, where the presentation instruction message carries the execution result and is used to instruct the third device to present the execution result, and the third device is a device, except the second device, that is discovered by the first device and to which the first device establishes a connection.

With reference to any one of the fifth aspect, or the first possible implementation manner to the third possible implementation manner of the fifth aspect, in a fourth possible implementation manner, the processor is further configured to determine that the user is in a second scene mode, where the second scene mode is a scene mode in which execution of the first application corresponding to the first scene mode is stopped; and if the execution device is the second device, the transmitter is further configured to send an instruction message for stopping the execution of the first application to the second device, so that the second device stops the execution of the first application.

With reference to any one of the fifth aspect, or the first possible implementation manner to the fourth possible implementation manner of the fifth aspect, in a fifth possible implementation manner, the processor is further configured to obtain information about a specific application that can be executed by the second device; and the processor is configured to determine, according to the preset execution policy corresponding to the first scene mode and information about a specific application that can be executed by the first device and the second device, the execution device of the first application corresponding to the first scene mode.

According to a sixth aspect, a second device is provided, including a communications module configured to be discovered by a first device and establish a connection to the first device by using a wireless communications technology, where the first device is a device that controls a specific application of the second device; a receiver configured to receive an instruction message sent by the first device and for executing a first application, where the first application is any specific application corresponding to a first scene mode; and a processor configured to execute the first application.

With reference to the sixth aspect, in a first possible implementation manner, if the execution device is the first device and the presentation device is the second device, the receiver is further configured to receive a presentation instruction message sent by the first device, where the presentation instruction message carries the execution result; and the second device further includes an output device configured to present the execution result; or if the execution device is the second device and the presentation device is the first device, the second device further includes a transmitter configured to send the execution result to the first device; or if the second device serves as both the execution device and the presentation device, the receiver is further configured to receive a presentation instruction message sent by the first device; and the second device further includes an output device configured to present the execution result; or if the execution device is the second device and the presentation device is a third device, the second device further includes a transmitter configured to send the execution result to the first device, so that the first device sends a presentation instruction message to the third device, where the presentation instruction message carries the execution result and is used to instruct the third device to present the execution result, and the third device is a device, except the second device, that is discovered by the first device and to which the first device establishes a connection; or if the execution device is the second device and the presentation device is a third device, the receiver is further configured to receive a sending instruction message sent by the first device, where the sending instruction message is used to instruct the second device to send the execution result to the third device; and the second device further includes a transmitter configured to send the execution result to the third device, so that the third device presents the execution result, where the third device is a device, except the second device, that is discovered by the first device and to which the first device establishes a connection.

With reference to the sixth aspect or the first possible implementation manner of the sixth aspect, in a second possible implementation manner, the receiver is further configured to receive an instruction message sent by the first device and for stopping execution of the first application; and the processor is further configured to stop the execution of the first application.

In the foregoing technical solutions, after determining that a user is in a scene mode, a first device can select an execution device for a specific application corresponding to the scene mode. Compared with some approaches in which when a user is in a scene mode, all devices that are carried by the user and can execute a specific application corresponding to the scene mode automatically execute the specific application, the present disclosure reduces total power consumed in a process of executing the specific application.

BRIEF DESCRIPTION OF DRAWINGS

To describe the technical solutions in the embodiments of the present disclosure or in some approaches more clearly, the following briefly describes the accompanying drawings for describing the embodiments or some approaches. The accompanying drawings in the following description show some embodiments of the present disclosure, and persons of ordinary skill in the art may still derive other drawings from these accompanying drawings without creative efforts.

DESCRIPTION OF EMBODIMENTS

The following clearly and completely describes the technical solutions in the embodiments of the present disclosure with reference to the accompanying drawings in the embodiments of the present disclosure. The described embodiments are merely some but not all of the embodiments of the present disclosure. All other embodiments obtained by persons of ordinary skill in the art based on the embodiments of the present disclosure without creative efforts shall fall within the protection scope of the present disclosure.

The term "and/or" in this specification describes only an association relationship for describing associated objects and represents that three relationships may exist. For example, A and/or B may represent the following three cases, only A exists, both A and B exist, and only B exists. In addition, the character "/" in this specification generally indicates an "or" relationship between the associated objects. In addition, the term "multiple" in this specification refers to two or more.

Embodiment 1

Figure 1:
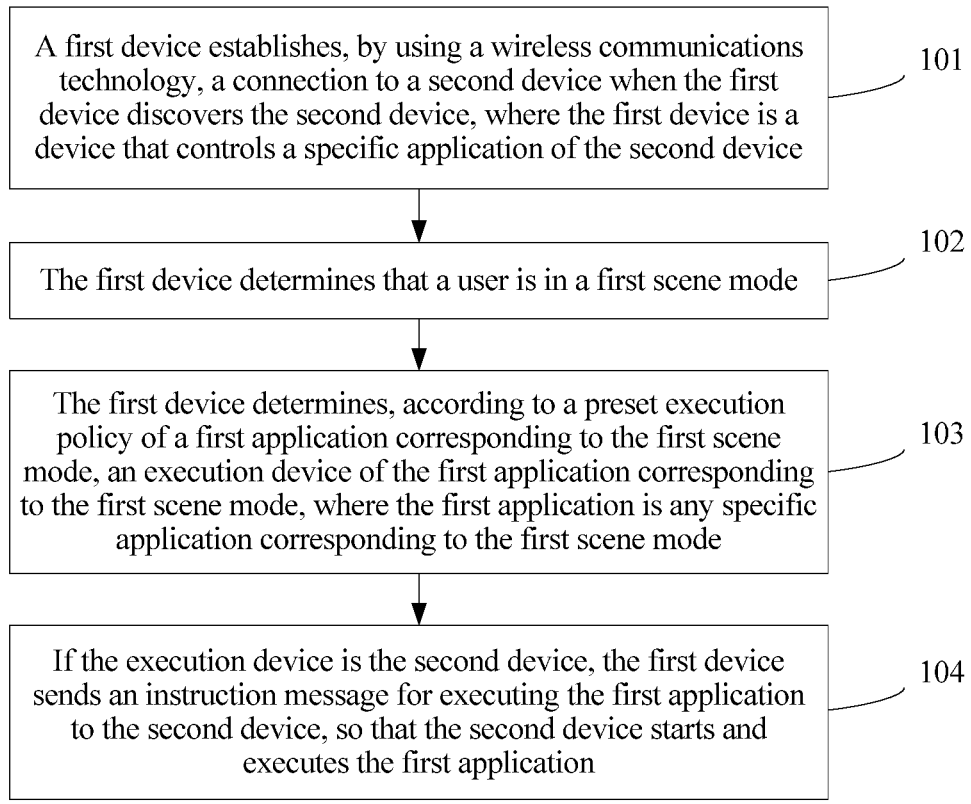
FIG. 1 is a flowchart of a portable device control method according to an embodiment of the present disclosure.

This embodiment of the present disclosure provides a portable device control method. As shown in FIG. 1, the method includes the following.

Step 101. A first device establishes, by using a wireless communications technology, a connection to a second device when the first device discovers the second device, where the first device is a device that controls a specific application of the second device.

A "portable device" (hereinafter referred to as a "device") in this embodiment of the present disclosure may be a wearable smart device, a mobile terminal, or the like, and may be a smart wrist watch, a smart band, a smart anklet, smart glasses, a smart phone, a tablet computer, a notebook computer, or the like.

The "first device" may be a device specified by a user, or may be a device chosen, among multiple devices in mutual communication, according to a preset first device policy. The preset first device policy may be a policy of determining, according to a use habit of a user or another rule, a priority order of a part or all of devices that are carried by the user and may be used as the first device, or may be another policy.

The first device may use a method in some approaches to discover the second device, for example, use a wireless communications technology to discover the second device. The wireless communications technology may be Worldwide Interoperability for Microwave Access, Long Term Evolution (LTE), Wireless Fidelity (Wi-Fi), and Bluetooth (BT), or the like. Optionally, the first device may use a short range wireless communications technology to discover the second device, where the short range wireless communications technology may be Wi-Fi, BT, ZigBee, Z-wave, ultra-wideband, infrared, or Near Field Communication, or the like.

The "specific application" may be an application (APP), a service, or a function of a device that can be executed by the device in a scene mode. The "specific application" may be a step counting application, a location application, a heart rate detection application, or the like.

That "the first device is a device that controls a specific application of the second device" may be understood as the first device may control execution, execution result presentation, execution stop, and the like of the specific application of the second device. A specific implementation manner in which the first device controls the specific application of the second device may be a control APP is installed on both the first device and the second device; the first device uses the control APP of the first device to send a control message to the control APP of the second device; and according to the control message received by the control APP of the second device, the second device executes a corresponding specific application, presents an execution result, stops execution of a corresponding specific application, or does the like. The first device and the second device may be devices carried by a same user, or may be devices carried by different users.

102. The first device determines that a user is in a first scene mode.

The "first scene mode" may be any one of statuses such as a motion status, a health detection status, and a sleep status. The motion status may include a walking state, a running state, and the like; the health detection status may include a heart rate detection state, a pulse detection state, a blood pressure detection state, and the like.

Step 102 may be implemented in any one of the following manners.

Manner 1, the first device determines, according to an indicator parameter detected by an induction apparatus of the first device, that the user is in the first scene mode, where the induction apparatus may be a Hall component, a gravity sensor, a tri-axis accelerometer, a gyroscope, or the like.

The first device may calculate an average moving rate v according to a real-time moving rate that is of the user and detected by the induction apparatus of the first device during a time period, and determine, according to v, that the user is in the motion status. For example, if $1.1 \leq v \leq 5.5$, that the user is in the motion status is determined, where if $1.1 \leq v < 1.4$, that the user is in the walking state is determined, or if $1.4 \leq v < 5.5$, that the user is in the running state is determined. The first device may determine, according to a change that is of a body indicator parameter of the user and that is detected by the induction apparatus of the first device, that the user is in the health detection status. For example, when the body indicator parameter is a heart rate, if a detected heart rate of the user does not fall within a preset healthy heart rate range, that the user is in the health detection status is determined. The first device may determine, according to a change of a bioelectricity signal of the user's body or stability of a heart rate/pulse of the user obtained by scanning by the induction apparatus of the first device, that the user is in a sleep state.

Manner 2, the first device determines, according to a preset time point or time period, that the user is in the first scene mode.

The first device may determine, when detecting that a current time point is a preset health detection time point, that the user is in the health detection status; or may determine, when detecting that a current time point falls within a preset sleep time period, that the user is in a sleep state.

In addition, the first device may further determine, according to an instruction from the user or a message received from another device, that the user is in the first scene mode.

103. The first device determines, according to a preset execution policy of a first application corresponding to the first scene mode, an execution device of the first application corresponding to the first scene mode, where the first application is any specific application corresponding to the first scene mode.

The "preset execution policy of the first application" may be a policy of determining the execution device according to a priority order of devices that execute the first application, may be a policy of determining the execution device according to an instruction from the user, or may be another policy. The "priority order of devices that execute the first application" may be determined according to a habit of the user or another rule. Preset execution policies of different first applications may be the same or different. The preset execution policy may be preset in the first device and/or another device that establishes a connection to the first device.

It should be noted that one scene mode may correspond to one or more specific applications. For example, specific applications corresponding to the motion status may be the step counting application and the location application, and a specific application corresponding to the heart rate detection state may be the heart rate detection application. When the first scene mode corresponds to multiple specific applications, the "first application corresponding to the first scene mode" may be any application in the multiple specific applications. If the first scene mode is the heart rate detection state of the user, a specific application corresponding to the first scene mode may be the heart rate detection application, and therefore the first scene mode may correspond to one first application, that is, the heart rate detection application; or if the first scene mode is the motion status of the user, specific applications corresponding to the first scene mode may be the step counting application and the location application, and therefore the first scene mode may correspond to two first applications, which are respectively the step counting application and the location application. In this case, the first device may determine one or more first applications corresponding to the first scene mode, and determine an execution device for each first application, where execution devices corresponding to different first applications may be the same or different.

It should be noted that when the first device determines that the user is in multiple first scene modes, in this case, the first device may determine one or more first applications corresponding to each first scene mode, and determine an execution device for the one or more first applications corresponding to each first scene mode. Execution devices corresponding to first applications of different first scene modes may be the same or different.

Optionally, before step 103, the method may further include obtaining, by the first device, information about a specific application that can be executed by the second device. In this case, step 103 may be the first device determines, according to a preset execution policy corresponding to the first scene mode and information about a specific application that can be executed by the first device and the second device, an execution device of the first application corresponding to the first scene mode.

104. If the execution device is the second device, the first device sends an instruction message for executing the first application to the second device, so that the second device executes the first application.

Optionally, after step 103, the method may further include determining, by the first device according to a preset presentation policy, a presentation device for an execution result of the first application. After step 104, the method may further include any step of the following steps (A) to (D).

Step (A), if the presentation device is the first device, the first device obtains the execution result from the second device, and the first device presents the execution result.

Step (B), if the presentation device is the second device, the first device sends a presentation instruction message to the second device, so that the second device presents the execution result.

Step (C), if the presentation device is a third device, the first device obtains the execution result from the second device, and sends a presentation instruction message to the third device, where the presentation instruction message carries the execution result and is used to instruct the third device to present the execution result. The third device is a device, except the second device, that is discovered by the first device and to which the first device establishes a connection. The third device and the first device may be devices carried by a same user, or may be devices carried by different users.

Step (D), if the presentation device is a third device, the first device sends a sending instruction message to the second device, and sends a presentation instruction message to the third device, where the sending instruction message is used to instruct the second device to send the execution result to the third device, and the presentation instruction message is used to instruct the third device to present the execution result. The third device is a device, except the second device, that is discovered by the first device and to which the first device establishes a connection. The third device and the first device may be devices carried by a same user, or may be devices carried by different users.

The "preset presentation policy" may be a policy of determining the presentation device according to a priority order of devices that present the execution result, may be a policy of determining the presentation device according to an instruction from the user, or may be another policy. The "priority order of devices that present the execution result" may be determined according to a habit of the user or another rule. Preset presentation policies of first applications corresponding to different scene modes may be the same or different. The preset presentation policy may be preset in the first device and/or another device that establishes a connection to the first device. A presentation manner of the "execution result" may include but is not limited to a text, a picture, audio, a video, or the like.

Optionally, the method may further include executing, by the first device, the first application if the execution device is the first device. In a possible implementation manner of this optional solution, if the execution device is the first device, the first device executes the first application, and the first device sends an instruction message for skipping executing the first application to the second device, so that the second device does not execute the first application. In this case, after step 103, the method may further include determining, by the first device according to a preset presentation policy, a presentation device for an execution result of the first application. After the first device executes the first application, the method may further include any step of the following steps (A) to (C).

Step (A), if the presentation device is the first device, the first device presents the execution result.

Step (B), if the presentation device is the second device, the first device sends a presentation instruction message to the second device, where the presentation instruction message carries the execution result, so that the second device presents the execution result.

Step (C), if the presentation device is a third device, the first device sends a presentation instruction message to the third device, where the presentation instruction message carries the execution result and is used to instruct the third device to present the execution result. The third device is a device, except the second device, that is discovered by the first device and to which the first device establishes a connection. The third device and the first device may be devices carried by a same user, or may be devices carried by different users.

Optionally, after step 104, the method may further include determining, by the first device, that the user is in a second scene mode, where the second scene mode is a scene mode in which execution of the first application corresponding to the first scene mode is stopped; and if the execution device is the second device, sending, by the first device, an instruction message for stopping the execution of the first application to the second device, so that the second device stops the execution of the first application. In addition, the first device stops the execution of the first application if the execution device is the first device.

According to the portable device control method provided in this embodiment, after determining that a user is in a scene mode, a first device can select an execution device for a specific application corresponding to the scene mode. Compared with some approaches in which when a user is in a scene mode, all devices that are carried by the user and can execute a specific application corresponding to the scene mode automatically execute the specific application, the present disclosure reduces total power consumed in a process of executing the specific application. In addition, compared with some approaches in which all the devices that are carried by the user and can execute the specific application corresponding to the scene mode present an execution result of the specific application executed by the devices, the present disclosure can avoid a problem of poor user experience caused by confusion of the user that an execution result presented on which device shall prevail.

Embodiment 2

Figure 2:
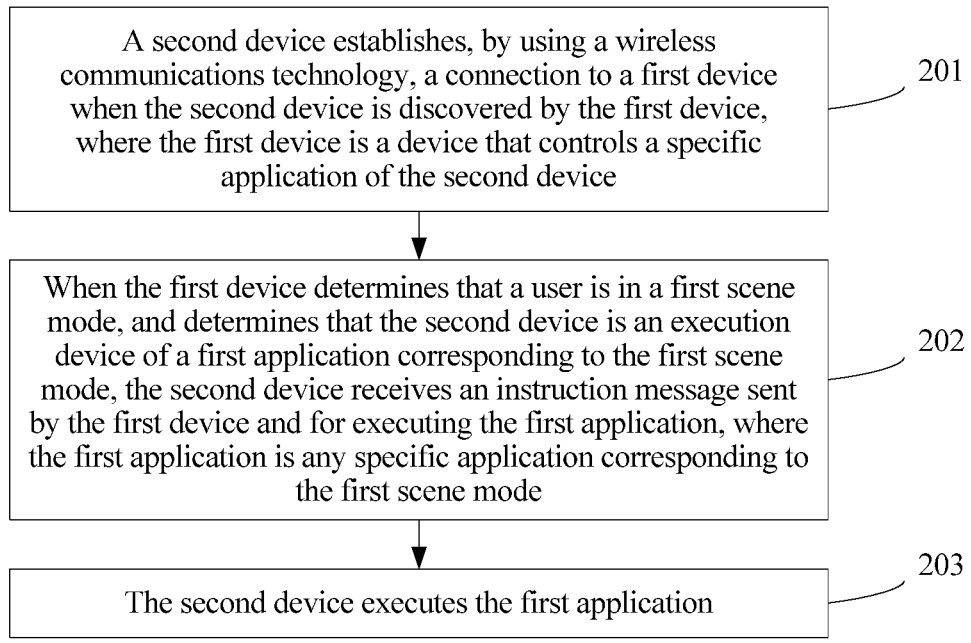
FIG. 2 is a flowchart of another portable device control method according to an embodiment of the present disclosure.

This embodiment of the present disclosure provides a portable device control method. As shown in FIG. 2, the method includes the following steps.

Step 201, a second device establishes, by using a wireless communications technology, a connection to a first device when the second device is discovered by the first device, where the first device is a device that controls a specific application of the second device.

The first device and the second device may be devices carried by a same user, or may be devices carried by different users.

202. When the first device determines that a user is in a first scene mode, and determines that the second device is an execution device of a first application corresponding to the first scene mode, the second device receives an instruction message sent by the first device and for executing the first application, where the first application is any specific application corresponding to the first scene mode.

203. The second device executes the first application.

Optionally, after step 203, the method may further include any step of the following steps (A) to (E).

Step (A), If the execution device is the first device and the presentation device is the second device, the second device receives a presentation instruction message sent by the first device, where the presentation instruction message carries an execution result, and the second device presents the execution result.

Step (B), if the execution device is the second device and the presentation device is the first device, the second device sends an execution result to the first device.

Step (C), if the second device serves as both the execution device and the presentation device, the second device receives a presentation instruction message sent by the first device, and the second device presents an execution result.

Step (D), if the execution device is the second device and the presentation device is a third device, the second device sends an execution result to the first device, so that the first device sends a presentation instruction message to the third device, where the presentation instruction message carries the execution result and is used to instruct the third device to present the execution result. The third device is a device, except the second device, that is discovered by the first device and to which the first device establishes a connection. The third device and the first device may be devices carried by a same user, or may be devices carried by different users.

Step (E), if the execution device is the second device and the presentation device is a third device, the second device receives a sending instruction message sent by the first device, where the sending instruction message is used to instruct the second device to send an execution result to the third device; and the second device sends the execution result to the third device, so that the third device presents the execution result. The third device is a device, except the second device, that is discovered by the first device and to which the first device establishes a connection. The third device and the first device may be devices carried by a same user, or may be devices carried by different users.

Optionally, before step 203, the method may further include determining, by the first device, that the user is in a second scene mode; if the second device is the execution device of the first application, receiving, by the second device, an instruction message sent by the first device and for stopping execution of the first application, where the second scene mode is a scene mode in which the execution of the first application corresponding to the first scene mode is stopped; and stopping, by the second device, the execution of the first application.

For related explanations in this embodiment, reference may be made to Embodiment 1.

According to the portable device control method provided in this embodiment, a second device can execute, under control of a first device, a specific application corresponding to a scene mode. Compared with some approaches in which when a user is in a scene mode, all devices that are carried by the user and can execute a specific application corresponding to the scene mode automatically execute the specific application, the present disclosure reduces total power consumed in a process of executing the specific application.

The following uses specific embodiments to illustrate the portable device control methods provided in Embodiment 1 and Embodiment 2.

Embodiment 1'

Figure 3A:
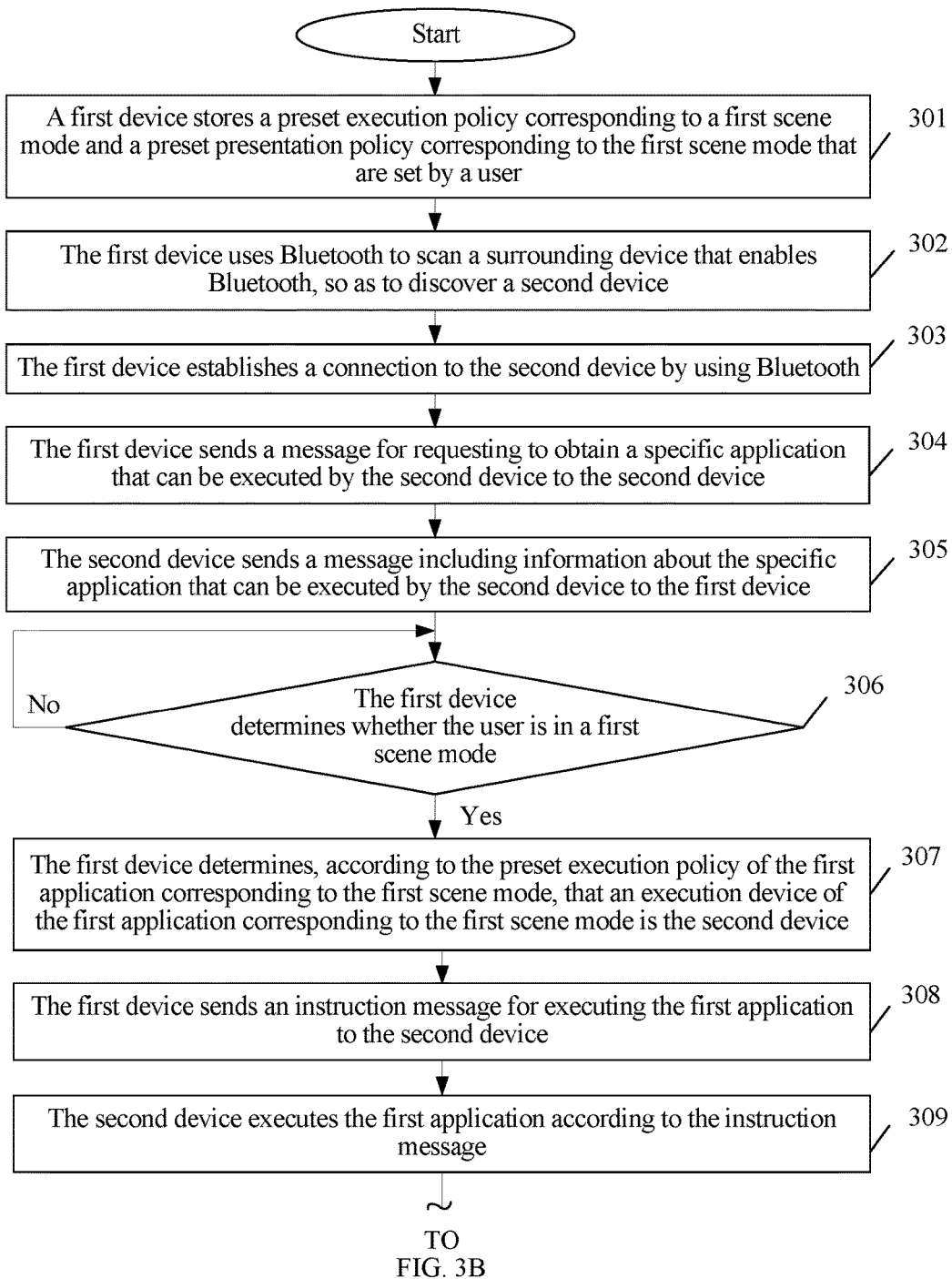
FIG. 3A and FIG. 3B are an interaction flowchart of a portable device control method according to an embodiment of the present disclosure.
Figure 3B:
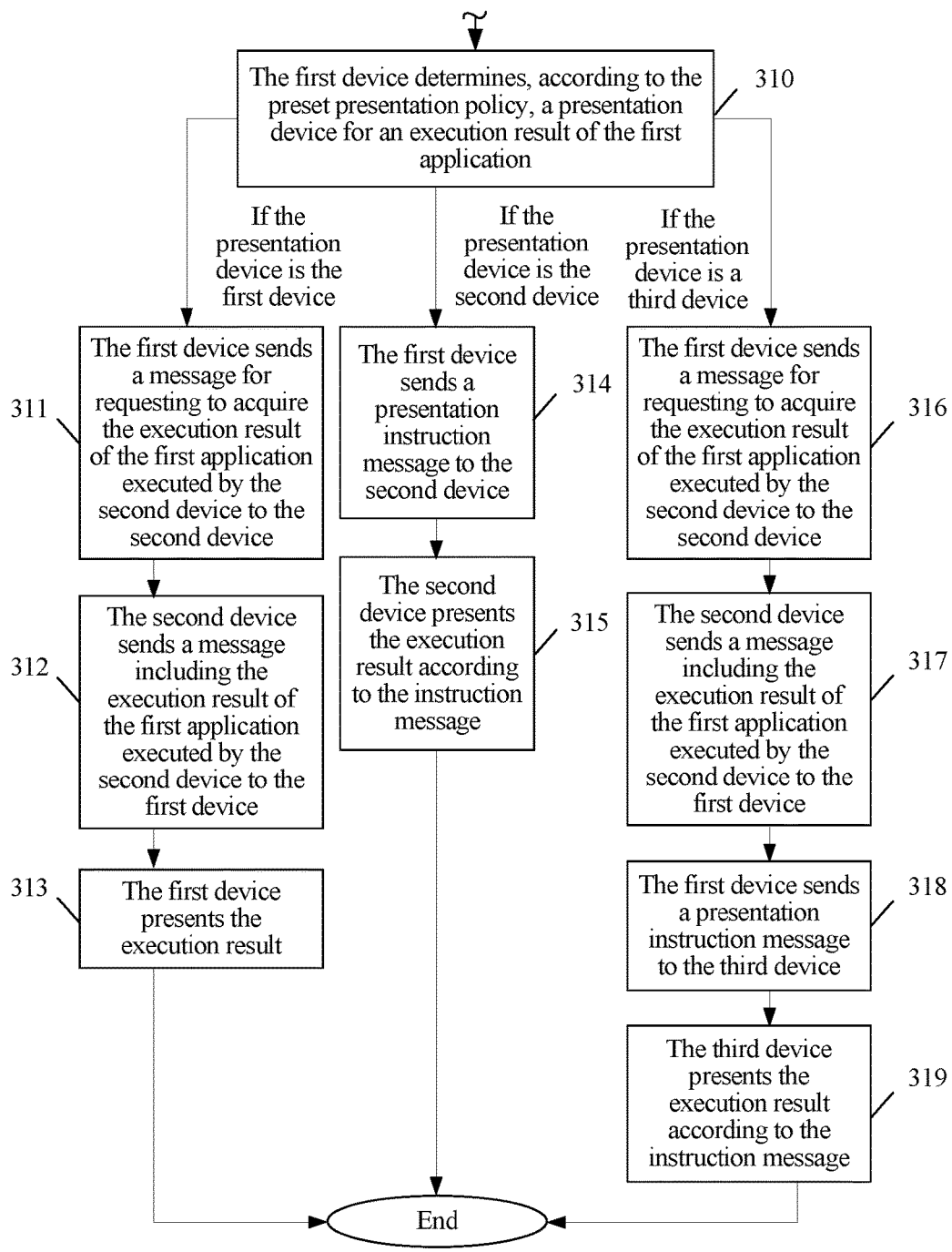

The "wireless communications technology" in Embodiment 1 and Embodiment 2 is BT in this embodiment, and the "execution device" is a second device in this embodiment. As shown in FIG. 3A and FIG. 3B, a portable device control method is provided in this embodiment, where the method includes the following steps.

Step 301, a first device stores a preset execution policy corresponding to a first scene mode and a preset presentation policy corresponding to the first scene mode that are set by a user.

302. The first device uses BT to scan a surrounding device that enables BT, so as to discover a second device.

The first device broadcasts a SCAN_REQ packet after receiving an ADV_IND packet broadcast by the surrounding device that enables BT, and a device that receives the SCAN_REQ packet feeds back a SCAN_RSP packet including information such as a BT address of the device to the first device. It should be noted that a device that feeds back a SCAN_RSP packet to the first device is a device discovered by the first device. Further, the first device may determine, according to a BT address in a SCAN_RSP packet fed back by each device, a device that is carried by a same user with the first device, that is, the second device.

303. The first device establishes a connection to the second device by using BT.

304. The first device sends a message for requesting to obtain a specific application that can be executed by the second device to the second device.

305. The second device sends a message including information about the specific application that can be executed by the second device to the first device.

306. The first device determines whether the user is in a first scene mode.

If the user is in the first scene mode, step 307 is performed; or if the user is not in the first scene mode, go back to step 306.

307. The first device determines, according to the preset execution policy of the first application corresponding to the first scene mode, that an execution device of the first application corresponding to the first scene mode is the second device.

308. The first device sends an instruction message for executing the first application to the second device.

309. The second device executes the first application according to the instruction message.

310. The first device determines, according to the preset presentation policy, a presentation device for an execution result of the first application.

If the presentation device is the first device, step 311 is performed; if the presentation device is the second device, step 314 is performed; or if the presentation device is a third device, step 316 is performed.

311. The first device sends a message for requesting to obtain the execution result of the first application executed by the second device to the second device.

312. The second device sends a message including the execution result of the first application executed by the second device to the first device.

313. The first device presents the execution result.

After step 313 is performed, a process ends.

314. The first device sends a presentation instruction message to the second device.

315. The second device presents the execution result according to the instruction message.

After step 315 is performed, a process ends.

316. The first device sends a message for requesting to obtain the execution result of the first application executed by the second device to the second device.

317. The second device sends a message including the execution result of the first application executed by the second device to the first device.

318. The first device sends a presentation instruction message to the third device, where the presentation instruction message carries the execution result of the first application executed by the second device, and the third device is a device, except the second device, that is discovered by the first device and to which the first device establishes a connection.

319. The third device presents the execution result according to the instruction message.

After step 319 is performed, a process ends.

Optionally, steps 316 to 319 may also be replaced by the following steps.

Step 316', the first device sends a sending instruction message to the second device, where the sending instruction message is used to instruct the second device to send the execution result of the first application executed by the second device to the third device.

317'. The second device sends, according to the sending instruction message, a message including the execution result to the third device, and sends a response message for the sending instruction message to the first device.

Optionally, step 317' may also be replaced by the following step, the second device sends, according to the sending instruction message, a message including the execution result to the third device, and the third device sends a response message for the message including the execution result to the first device.

318'. The first device sends a presentation instruction message to the third device.

319'. The third device presents the execution result according to the instruction message.

After step 319' is performed, a process ends.

Optionally, after step 309, the method may further include sending, by the first device when determining that the user is in a second scene mode, an instruction message for stopping the execution of the first application to the second device; and stopping, by the second device, the execution of the first application according to the instruction message.

According to the portable device control method provided in this embodiment, after determining that a user is in a scene mode, a first device can select an execution device and a presentation device for a specific application corresponding to the scene mode. Compared with some approaches in which when a user is in a scene mode, all devices that are carried by the user and can execute a specific application corresponding to the scene mode automatically execute the specific application, the present disclosure reduces total power consumed in a process of executing the specific application. In addition, compared with some approaches in which all the devices that are carried by the user and can execute the specific application corresponding to the scene mode present an execution result of the specific application executed by the devices, the present disclosure can avoid a problem of poor user experience caused by confusion of the user that an execution result presented on which device shall prevail.

Embodiment 2'

Figure 4A:
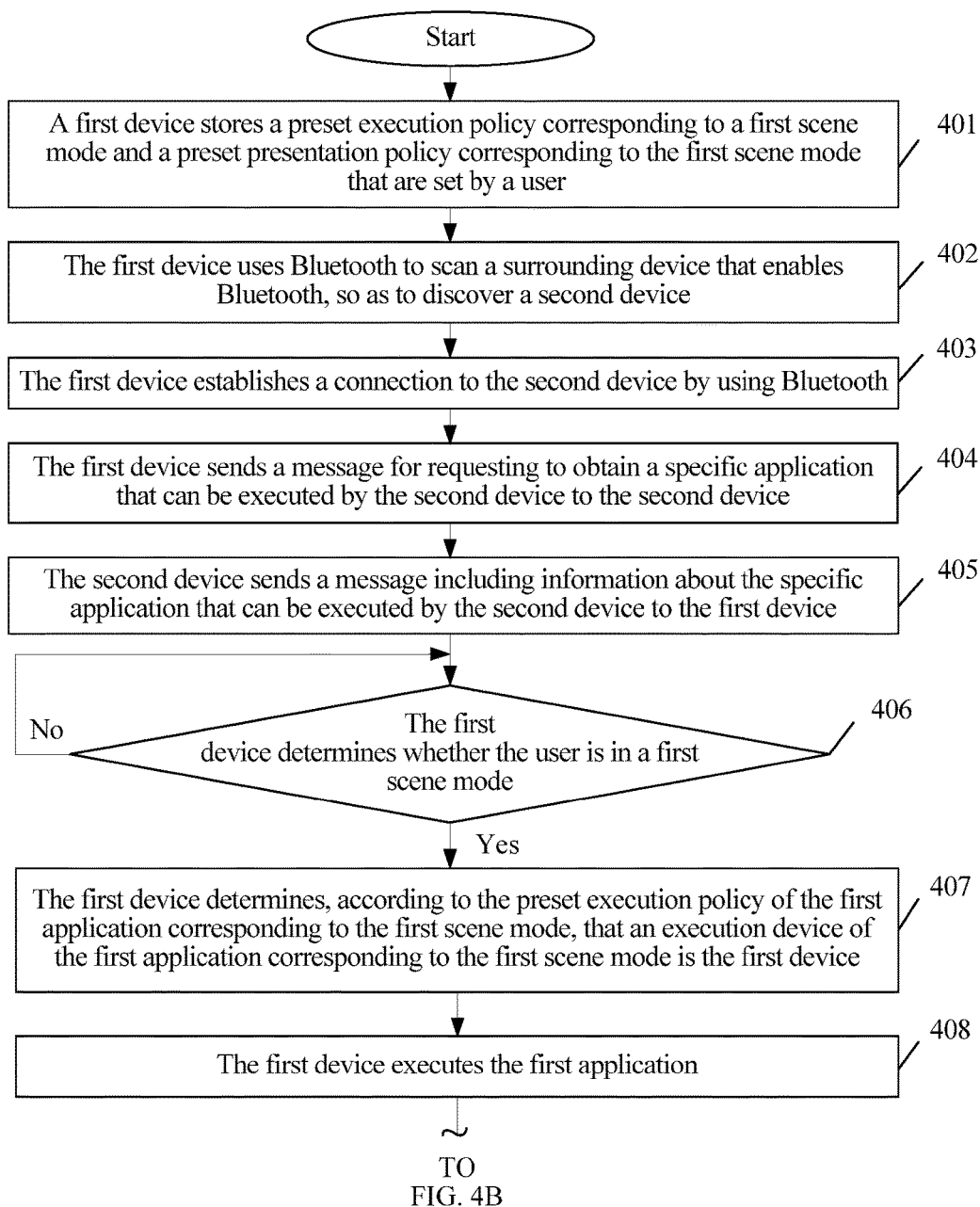
FIG. 4A and FIG. 4B are an interaction flowchart of another portable device control method according to an embodiment of the present disclosure.
Figure 4B:
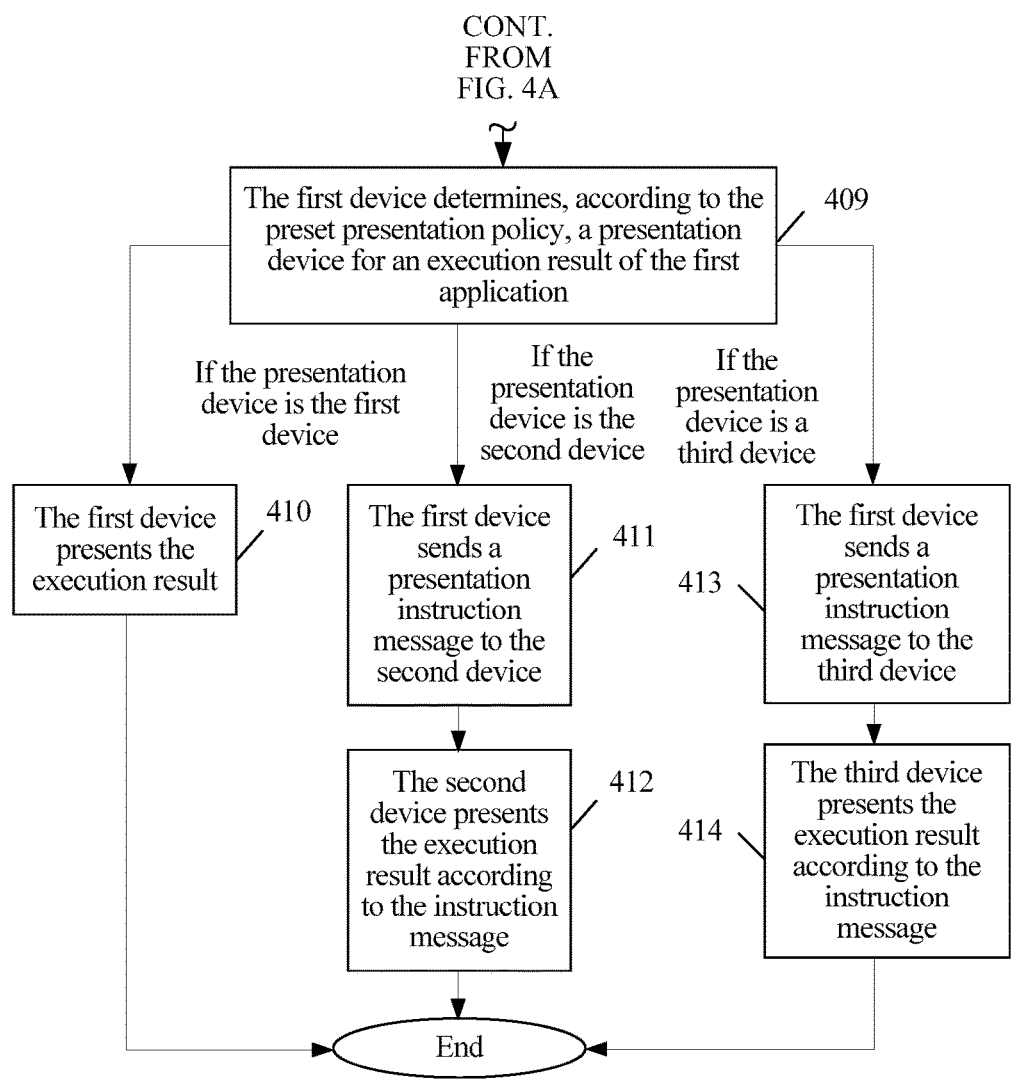

The "wireless communications technology" in Embodiment 1 and Embodiment 2 is BT in this embodiment, and the "execution device" is a first device in this embodiment. As shown in FIG. 4A and FIG. 4B, a portable device control method is provided in this embodiment, where the method includes the following steps.

Steps 401 to 405 are the same as steps 301 to 305 in Embodiment 1'.

406. The first device determines whether the user is in a first scene mode.

If the user is in the first scene mode, step 407 is performed; or if the user is not in the first scene mode, go back to step 406.

407. The first device determines, according to the preset execution policy of the first application corresponding to the first scene mode, that an execution device of the first application corresponding to the first scene mode is the first device.

408. The first device executes the first application.

409. The first device determines, according to the preset presentation policy, a presentation device for an execution result of the first application.

If the presentation device is the first device, step 410 is performed; if the presentation device is the second device, step 411 is performed; or if the presentation device is a third device, step 413 is performed.

410. The first device presents the execution result.

After step 410 is performed, a process ends.

411. The first device sends a presentation instruction message to the second device, where the presentation instruction message carries the execution result of the first application executed by the first device.

412. The second device presents the execution result according to the instruction message.

After step 412 is performed, a process ends.

413. The first device sends a presentation instruction message to the third device, where the presentation instruction message carries the execution result of the first application executed by the first device, and the third device is a device, except the second device, that is discovered by the first device and to which the first device establishes a connection.

414. The third device presents the execution result according to the instruction message.

After step 414 is performed, a process ends.

Optionally, after step 408, the method may further include stopping, by the first device when determining that the user is in a second scene mode, the execution of the first application.

According to the portable device control method provided in this embodiment, after determining that a user is in a scene mode, a first device can select an execution device and a presentation device for a specific application corresponding to the scene mode. Compared with some approaches in which when a user is in a scene mode, all devices that are carried by the user and can execute a specific application corresponding to the scene mode automatically execute the specific application, the present disclosure reduces total power consumed in a process of executing the specific application. In addition, compared with some approaches in which all the devices that are carried by the user and can execute the specific application corresponding to the scene mode present an execution result of the specific application executed by the devices, the present disclosure can avoid a problem of poor user experience caused by confusion of the user that an execution result presented on which device shall prevail.

Embodiment 3'

Figure 5:
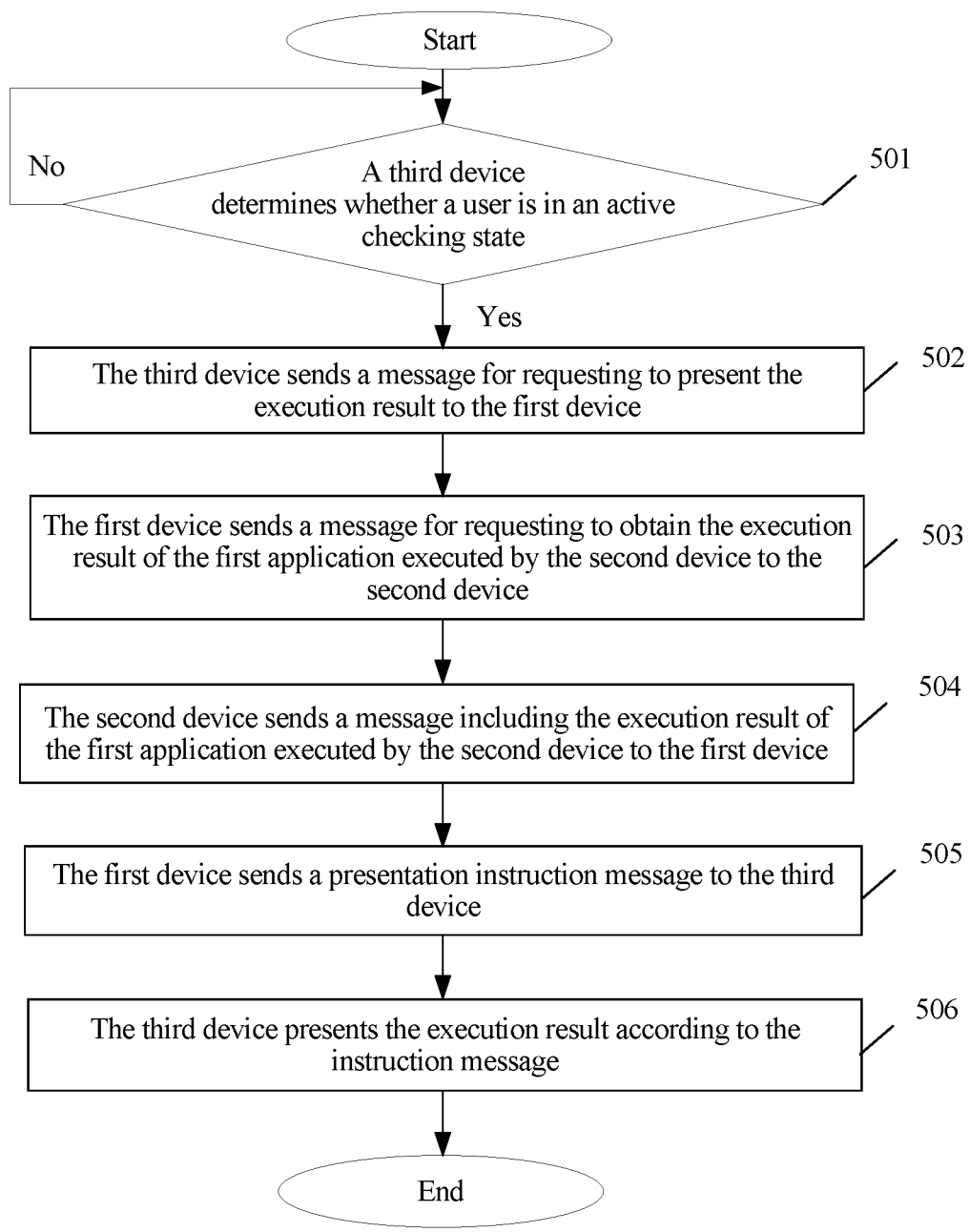
FIG. 5 is an interaction flowchart of another portable device control method according to an embodiment of the present disclosure.

Any device, which has a function of detecting an active checking state of a user, of a first device or a device that establishes a connection to the first device may detect whether the user is in the active checking state. A portable device control method provided in this embodiment is applied to a scenario in which a user actively checks an execution result of an execution device. This embodiment is described by using an example in which a "device that has a function of detecting an active checking state of a user" is a third device, an "execution device" is a second device, and the third device uses the first device to obtain an execution result of a first application executed by the second device. As shown in FIG. 5, a portable device control method is provided in this embodiment, where the method includes the following steps.

Step 501, the third device determines whether the user is in the active checking state.

If the user is in the active checking state, step 502 is performed; or if the user is not in the active checking state, go back to step 501.

Step 501 may be implemented in the following manner the third device determines that the user is in the active checking state when detecting, by using an induction apparatus of the third device, that an angle formed by a display interface of the third device and a horizontal direction falls within a specific range (for example, within 30 degrees), and that an angle formed by a sight line of the user and a perpendicular direction of the display interface falls within a specific range (for example, 60-120 degrees).

502. The third device sends a message for requesting to present the execution result to the first device.

503. The first device sends a message for requesting to obtain the execution result of the first application executed by the second device to the second device.

504. The second device sends a message including the execution result of the first application executed by the second device to the first device.

If the second device is executing a first application when the second device receives a request message sent by the first device, the second device sends a message including an execution result of the first application that is being executed to the first device; if the second device does not execute any application when the second device receives a request message sent by the first device, but stores an execution result of an executed first application in a preset storage time period, the second device sends a message including the execution result of the executed first application stored in the preset storage time period to the first device; or if the second device does not execute any application when the second device receives a request message sent by the first device, and stores no execution result of an executed specific application in a preset storage time period, the second device sends an empty message with no execution result to the first device.

505. The first device sends a presentation instruction message to the third device, where the presentation instruction message carries the execution result of the first application executed by the second device.

If the message sent by the second device to the first device is the empty message with no execution result, the presentation instruction message sent by the first device to the third device carries no execution result.

506. The third device presents the execution result according to the instruction message.

After step 506 is performed, a process ends.

In the example of step 505, the display interface of the third device may present no execution result, or may present words such as "no execution result", or the like.

Optionally, step 502 may be replaced by the following steps.

Step 502a, the third device sends a message including information about the user in the active checking state to the first device.

502b. The first device determines, according to the message, whether the user is in the active checking state.

According to the portable device control method provided in this embodiment, a device that can actively check a user state can present an execution result in time after determining that a user is in an active checking state, which meets a personalized requirement of the user, thereby improving user experience.

Embodiment 3

Figure 6:
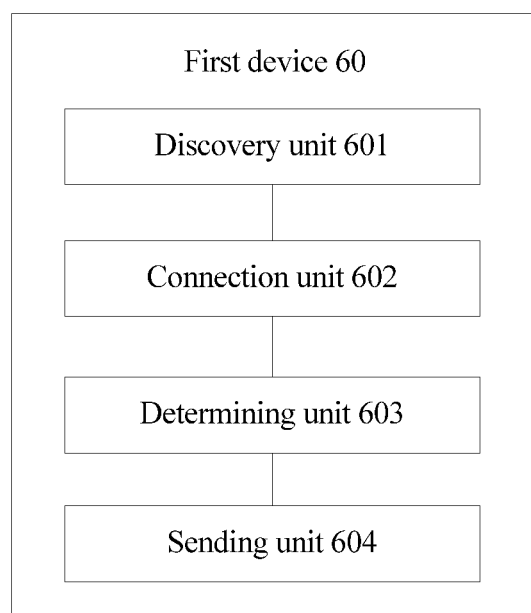
FIG. 6 is a schematic structural diagram of a first device according to an embodiment of the present disclosure.

This embodiment of the present disclosure provides a first device 60. As shown in FIG. 6, the first device 60 includes a discovery unit 601, a connection unit 602, a determining unit 603, and a sending unit 604.

The discovery unit 601 is configured to discover a second device, where the first device 60 is a device that controls a specific application of the second device. The first device 60 and the second device may be devices carried by a same user, or may be devices carried by different users.

The connection unit 602 is configured to establish a connection to the second device by using a wireless communications technology.

The determining unit 603 is configured to determine that a user is in a first scene mode, and determine, according to a preset execution policy of a first application corresponding to the first scene mode, an execution device of the first application corresponding to the first scene mode, where the first application is any specific application corresponding to the first scene mode.

The sending unit 604 is configured to, if the execution device is the second device, send an instruction message for executing the first application to the second device, so that the second device executes the first application.

Optionally, the determining unit 603 is further configured to determine, according to a preset presentation policy, a presentation device for an execution result of the first application.

Figure 7:
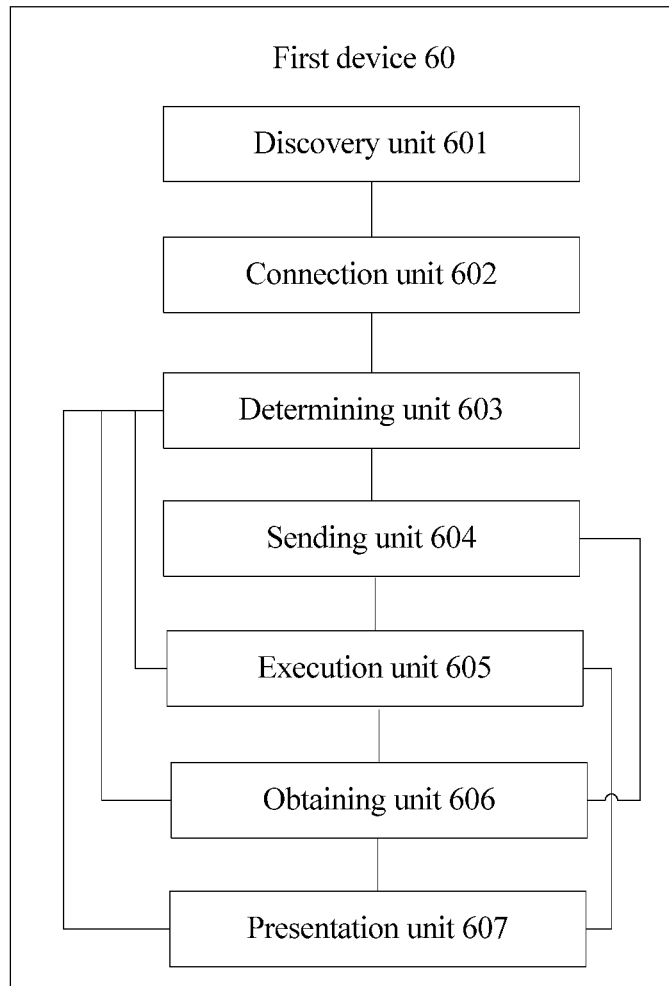
FIG. 7 is a schematic structural diagram of another first device according to an embodiment of the present disclosure.

If the presentation device is the first device 60, as shown in FIG. 7, the first device 60 further includes an obtaining unit 606 and a presentation unit 607, where the obtaining unit 606 is configured to obtain the execution result from the second device, and the presentation unit 607 is configured to present the execution result.

Alternatively, if the presentation device is the second device, the sending unit 604 is further configured to send a presentation instruction message to the second device, so that the second device presents the execution result.

Alternatively, if the presentation device is a third device, as shown in FIG. 7, the first device 60 further includes an obtaining unit 606 configured to obtain the execution result from the second device. The sending unit 604 is further configured to send a presentation instruction message to the third device, where the presentation instruction message carries the execution result and is used to instruct the third device to present the execution result. The third device is a device, except the second device, that is discovered by the first device 60 and to which the first device 60 establishes a connection. The third device and the first device 60 may be devices carried by a same user, or may be devices carried by different users.

Alternatively, if the presentation device is a third device, the sending unit 604 is further configured to send a sending instruction message to the second device, and send a presentation instruction message to the third device, where the sending instruction message is used to instruct the second device to send the execution result to the third device, and the presentation instruction message is used to instruct the third device to present the execution result. The third device is a device, except the second device, that is discovered by the first device 60 and to which the first device 60 establishes a connection. The third device and the first device 60 may be devices carried by a same user, or may be devices carried by different users.

Optionally, as shown in FIG. 7, the first device 60 further includes an execution unit 605 configured to execute the first application if the execution device is the first device 60.

In this case, the sending unit 604 is further configured to, if the execution device is the first device 60, send an instruction message for skipping executing the first application to the second device, so that the second device does not execute the first application.

In this case, the determining unit 603 is further configured to determine, according to a preset presentation policy, a presentation device for an execution result of the first application.

If the presentation device is the first device 60, as shown in FIG. 7, the first device 60 further includes a presentation unit 607 configured to present the execution result.

Alternatively, if the presentation device is the second device, the sending unit 604 is further configured to send a presentation instruction message to the second device, where the presentation instruction message carries the execution result, so that the second device presents the execution result.

Alternatively, if the presentation device is a third device, the sending unit 604 is further configured to send a presentation instruction message to the third device, where the presentation instruction message carries the execution result, so that the third device presents the execution result. The third device is a device, except the second device, that is discovered by the first device 60 and to which the first device 60 establishes a connection. The third device and the first device 60 may be devices carried by a same user, or may be devices carried by different users.

Optionally, the determining unit 603 is further configured to determine that the user is in a second scene mode, where the second scene mode is a scene mode in which execution of the first application corresponding to the first scene mode is stopped. In this case, the sending unit 604 is further configured to, if the execution device is the second device, send an instruction message for stopping the execution of the first application to the second device, so that the second device stops the execution of the first application. In addition, the execution unit 605 is further configured to stop the execution of the first application if the execution device is the first device 60.

Optionally, the obtaining unit 606 is further configured to obtain information about a specific application that can be executed by the second device; and the determining unit 603 is configured to determine, according to the preset execution policy corresponding to the first scene mode and information about a specific application that can be executed by the first device 60 and the second device, the execution device of the first application corresponding to the first scene mode.

It should be noted that the first device provided in this embodiment can be used to execute the portable device control method shown in the foregoing Embodiment 1. Therefore, for related explanations in this embodiment, reference may be made to Embodiment 1.

After determining that a user is in a scene mode, the first device provided in this embodiment can select an execution device for a specific application corresponding to the scene mode. Compared with some approaches in which when a user is in a scene mode, all devices that are carried by the user and can execute a specific application corresponding to the scene mode automatically execute the specific application, the present disclosure reduces total power consumed in a process of executing the specific application. In addition, compared with some approaches in which all the devices that are carried by the user and can execute the specific application corresponding to the scene mode present an execution result of the specific application executed by the devices, the present disclosure can avoid a problem of poor user experience caused by confusion of the user that an execution result presented on which device shall prevail.

Embodiment 4

Figure 8:
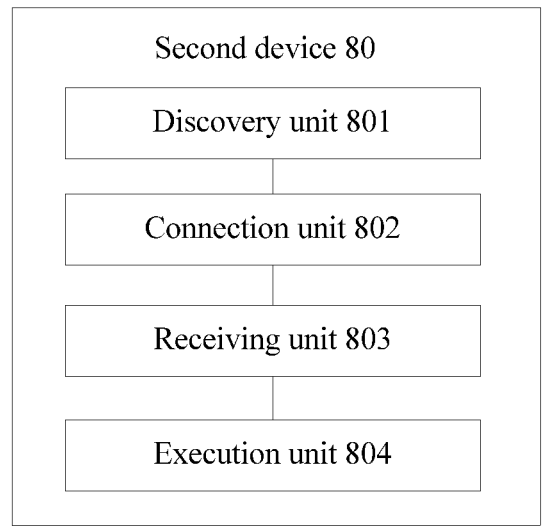
FIG. 8 is a schematic structural diagram of a second device according to an embodiment of the present disclosure.

This embodiment of the present disclosure provides a second device 80. As shown in FIG. 8, the second device 80 includes a discovery unit 801, a connection unit 802, a receiving unit 803, and an execution unit 804.

The discovery unit 801 is configured to be discovered by a first device, where the first device is a device that controls a specific application of the second device 80. The first device and the second device 80 may be devices carried by a same user, or may be devices carried by different users.

The connection unit 802 is configured to establish a connection to the first device by using a wireless communications technology.

The receiving unit 803 is configured to receive an instruction message sent by the first device and for executing a first application, where the first application is any specific application corresponding to a first scene mode.

The execution unit 804 is configured to execute the first application.

Figure 9:
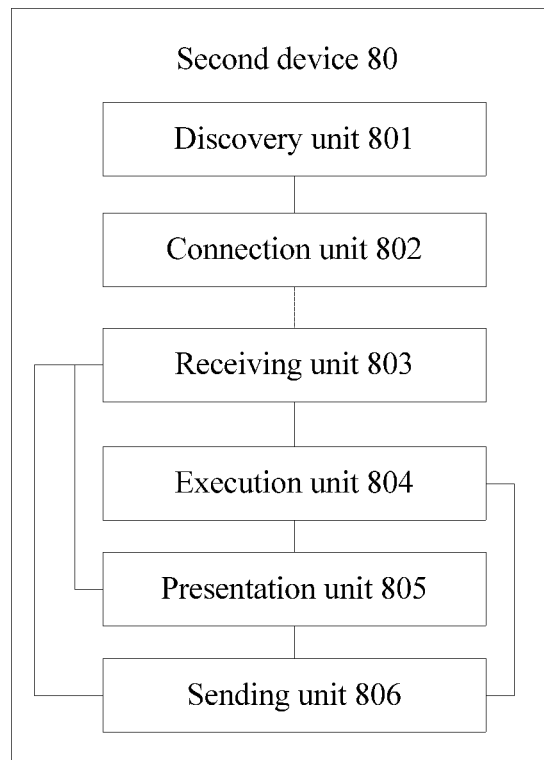
FIG. 9 is a schematic structural diagram of another second device according to an embodiment of the present disclosure.

Optionally, if the execution device is the first device and the presentation device is the second device 80, the receiving unit 803 is further configured to receive a presentation instruction message sent by the first device, where the presentation instruction message carries an execution result. As shown in FIG. 9, the second device 80 further includes a presentation unit 805 configured to present the execution result.

Alternatively, if the execution device is the second device 80 and the presentation device is the first device, as shown in FIG. 9, the second device 80 further includes a sending unit 806 configured to send an execution result to the first device.

Alternatively, if the second device 80 serves as both the execution device and the presentation device, the receiving unit 803 is further configured to receive a presentation instruction message sent by the first device. As shown in FIG. 9, the second device 80 further includes a presentation unit 805 configured to present an execution result.

Alternatively, if the execution device is the second device 80 and the presentation device is a third device, as shown in FIG. 9, the second device 80 further includes a sending unit 806 configured to send an execution result to the first device, so that the first device sends a presentation instruction message to the third device, where the presentation instruction message carries the execution result and is used to instruct the third device to present the execution result. The third device is a device, except the second device, that is discovered by the first device and to which the first device establishes a connection. The third device and the first device may be devices carried by a same user, or may be devices carried by different users.

Alternatively, if the execution device is the second device and the presentation device is a third device, the receiving unit 803 is further configured to receive a sending instruction message sent by the first device, where the sending instruction message is used to instruct the second device to send an execution result to the third device. As shown in FIG. 9, the second device 80 further includes a sending unit 806 configured to send the execution result to the third device, so that the third device presents the execution result. The third device is a device, except the second device, that is discovered by the first device and to which the first device establishes a connection. The third device and the first device may be devices carried by a same user, or may be devices carried by different users.

Optionally, the receiving unit 803 is further configured to receive an instruction message sent by the first device and for stopping execution of the first application; and the execution unit 804 is further configured to stop the execution of the first application.

It should be noted that the second device provided in this embodiment can be used to execute the portable device control method shown in the foregoing Embodiment 2. Therefore, for related explanations in this embodiment, reference may be made to Embodiment 2.

The second device provided in this embodiment can execute, under control of a first device, a specific application corresponding to a scene mode. Compared with some approaches in which when a user is in a scene mode, all devices that are carried by the user and can execute a specific application corresponding to the scene mode automatically execute the specific application, the present disclosure reduces total power consumed in a process of executing the specific application.

Embodiment 5

Figure 10:
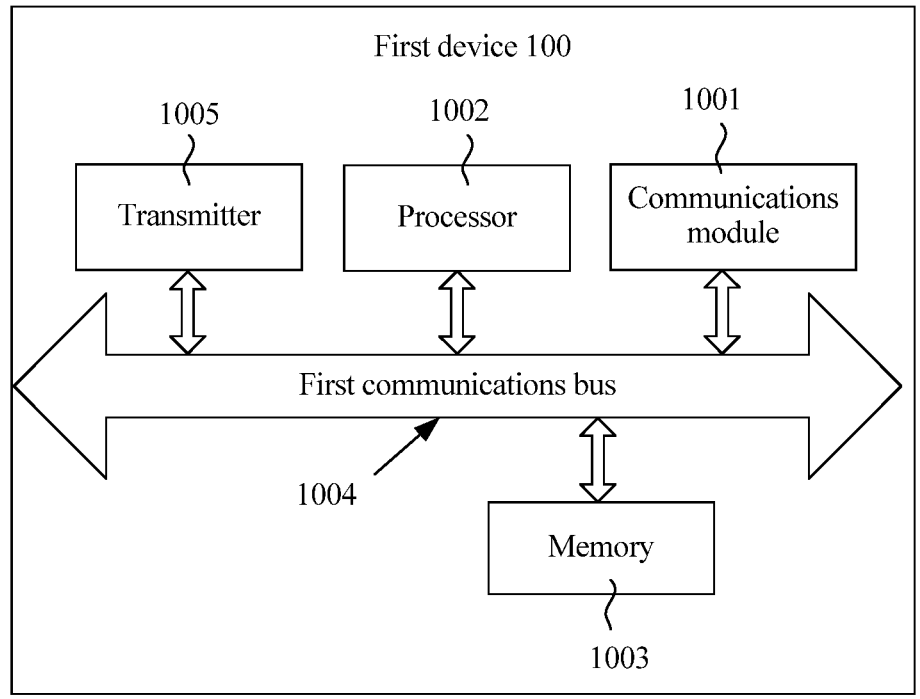
FIG. 10 is a schematic structural diagram of another first device according to an embodiment of the present disclosure.

This embodiment of the present disclosure provides a first device 100, where the first device 100 includes a communications module 1001, a processor 1002, a memory 1003, a first communications bus 1004, and a transmitter 1005, as shown in FIG. 10.

The processor 1002 may be a central processing unit (CPU), or an application-specific integrated circuit (ASIC), or be configured to be one or more integrated circuits implementing the embodiments the present disclosure.

The processor 1002 is configured to execute executable program code stored in the memory 1003, such as a computer program, so as to run a program corresponding to the executable code.

The memory 1003 is configured to store executable program code, where the program code includes a computer operation instruction. The memory 1003 may include a high-speed random access memory (RAM), and may further include a non-volatile memory, such as at least one disk memory.

The first communications bus 1004 may be an industry standard architecture (ISA) bus, a peripheral component interconnect (PCI) bus, an extended industry standard architecture (EISA) bus, or the like. The bus 1004 may be categorized into an address bus, a data bus, a control bus, and the like. For ease of denotation, the bus is indicated by using only one thick line in FIG. 10; however, it does not indicate that there is only one bus or only one type of bus.

The communications module 1001 is configured to establish a communication channel, so that an electrical device connects to or interacts with the outside by using the communication channel. The communications module 1001 may be a module that includes one or a combination of the following, a wireless local network module, a BT module, a baseband module, and the like, and a corresponding radio frequency circuit (configured to implement wireless local area network communication, BT communication, infrared communication, and/or cellular communications system communication).

The communications module 1001 is configured to discover a second device and establish a connection to the second device by using a wireless communications technology. The first device 100 is a device that controls a specific application of the second device. The first device 100 and the second device may be devices carried by a same user, or may be devices carried by different users.

The processor 1002 is configured to determine that a user is in a first scene mode, and determine, according to a preset execution policy of a first application corresponding to the first scene mode, an execution device of the first application corresponding to the first scene mode, where the first application is any specific application corresponding to the first scene mode.

The transmitter 1005 is configured to, if the execution device is the second device, send an instruction message for executing the first application to the second device, so that the second device executes the first application.

Optionally, the processor 1002 is further configured to determine, according to a preset presentation policy, a presentation device for an execution result of the first application.

Figure 11:
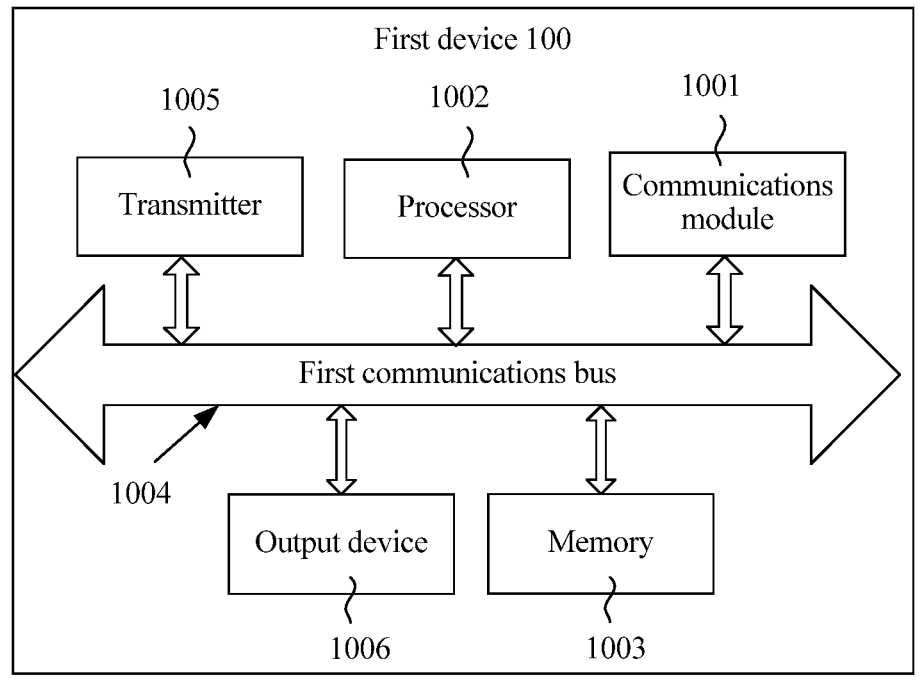
FIG. 11 is a schematic structural diagram of another first device according to an embodiment of the present disclosure.

If the presentation device is the first device 100, the processor 1002 is further configured to obtain the execution result from the second device. As shown in FIG. 11, the first device 100 further includes an output device 1006 configured to present the execution result. The output device 1006 may include but is not limited to a display screen, a speaker, and the like. An output manner of the output device 1006 may include but is not limited to a text, a picture, audio, a video, or the like.

Alternatively, if the presentation device is the second device, the transmitter 1005 is further configured to send a presentation instruction message to the second device, so that the second device presents the execution result.

Alternatively, if the presentation device is a third device, the processor 1002 is further configured to obtain the execution result from the second device, and the transmitter 1005 is further configured to send a presentation instruction message to the third device, where the presentation instruction message carries the execution result and is used to instruct the third device to present the execution result. The third device is a device, except the second device, that is discovered by the first device 100 and to which the first device 100 establishes a connection. The third device and the first device 100 may be devices carried by a same user, or may be devices carried by different users.

Alternatively, if the presentation device is a third device, the transmitter 1005 is further configured to send a sending instruction message to the second device, and send a presentation instruction message to the third device, where the sending instruction message is used to instruct the second device to send the execution result to the third device, and the presentation instruction message is used to instruct the third device to present the execution result. The third device is a device, except the second device, that is discovered by the first device 100 and to which the first device 100 establishes a connection. The third device and the first device 100 may be devices carried by a same user, or may be devices carried by different users.

Optionally, the processor 1002 is further configured to execute the first application if the execution device is the first device 100. In this case, the transmitter 1005 is further configured to, if the execution device is the first device 100, send an instruction message for skipping executing the first application to the second device, so that the second device does not execute the first application.

In this case, the processor 1002 is further configured to determine, according to a preset presentation policy, a presentation device for an execution result of the first application.

If the presentation device is the first device 100, as shown in FIG. 11, the first device 100 further includes an output device 1006 configured to present the execution result. The output device 1006 may include but is not limited to a display screen, a speaker, and the like. An output manner of the output device 1006 may include but is not limited to, a text, a picture, audio, a video, or the like.

Alternatively, if the presentation device is the second device, the transmitter 1005 is further configured to send a presentation instruction message to the second device, where the presentation instruction message carries the execution result, so that the second device presents the execution result.

Alternatively, if the presentation device is a third device, the transmitter 1005 is further configured to send a presentation instruction message to the third device, where the presentation instruction message carries the execution result and is used to instruct the third device to present the execution result. The third device is a device, except the second device, that is discovered by the first device 100 and to which the first device 100 establishes a connection. The third device and the first device 100 may be devices carried by a same user, or may be devices carried by different users.

Optionally, the processor 1002 is further configured to determine that the user is in a second scene mode, where the second scene mode is a scene mode in which execution of the first application corresponding to the first scene mode is stopped. In this case, the transmitter 1005 is further configured to, if the execution device is the second device, send an instruction message for stopping the execution of the first application to the second device, so that the second device stops the execution of the first application. In addition, the processor 1002 is further configured to stop the execution of the first application if the execution device is the first device 100.

Optionally, the processor 1002 is further configured to obtain information about a specific application that can be executed by the second device; and the processor 1002 is configured to determine, according to the preset execution policy corresponding to the first scene mode and information about a specific application that can be executed by the first device 100 and the second device, the execution device of the first application corresponding to the first scene mode.

It should be noted that the first device provided in this embodiment can be used to execute the portable device control method shown in the foregoing Embodiment 1. Therefore, for related explanations in this embodiment, reference may be made to Embodiment 1.

After determining that a user is in a scene mode, the first device provided in this embodiment can select an execution device for a specific application corresponding to the scene mode. Compared with some approaches in which when a user is in a scene mode, all devices that are carried by the user and can execute a specific application corresponding to the scene mode automatically execute the specific application, the present disclosure reduces total power consumed in a process of executing the specific application. In addition, compared with some approaches in which all the devices that are carried by the user and can execute the specific application corresponding to the scene mode present an execution result of the specific application executed by the devices, the present disclosure can avoid a problem of poor user experience caused by confusion of the user that an execution result presented on which device shall prevail.

Embodiment 6

Figure 12:
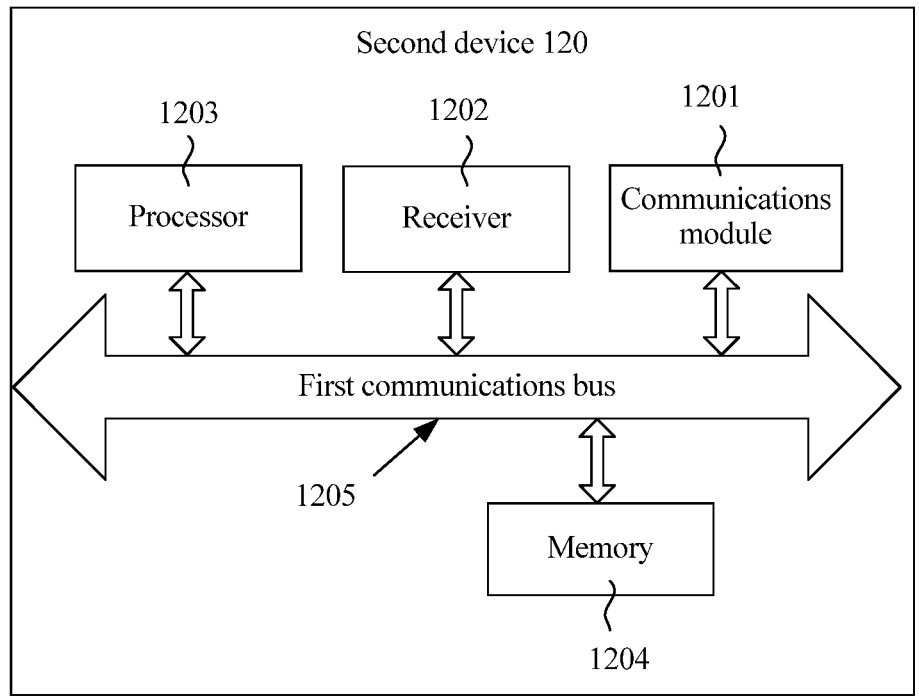
FIG. 12 is a schematic structural diagram of another second device according to an embodiment of the present disclosure.

This embodiment of the present disclosure provides a second device 120. As shown in FIG. 12, the second device 120 includes a communications module 1201, a receiver 1202, a processor 1203, a memory 1204, and a first communications bus 1205. For specific description of the communications module 1201, the processor 1203, the memory 1204, and the first communications bus 1205, reference may be made to the description of the communications module 1001, the processor 1002, the memory 1003, and the first communications bus 1004 in the foregoing Embodiment 5.

The communications module 1201 is further configured to be discovered by a first device and establish a connection to the first device by using a wireless communications technology. The first device is a device that controls a specific application of the second device 120. The first device and the second device 120 may be devices carried by a same user, or may be devices carried by different users.

The receiver 1202 is configured to receive an instruction message sent by the first device and for executing a first application, where the first application is any specific application corresponding to a first scene mode.

The processor 1203 is configured to execute the first application.

Figure 13:
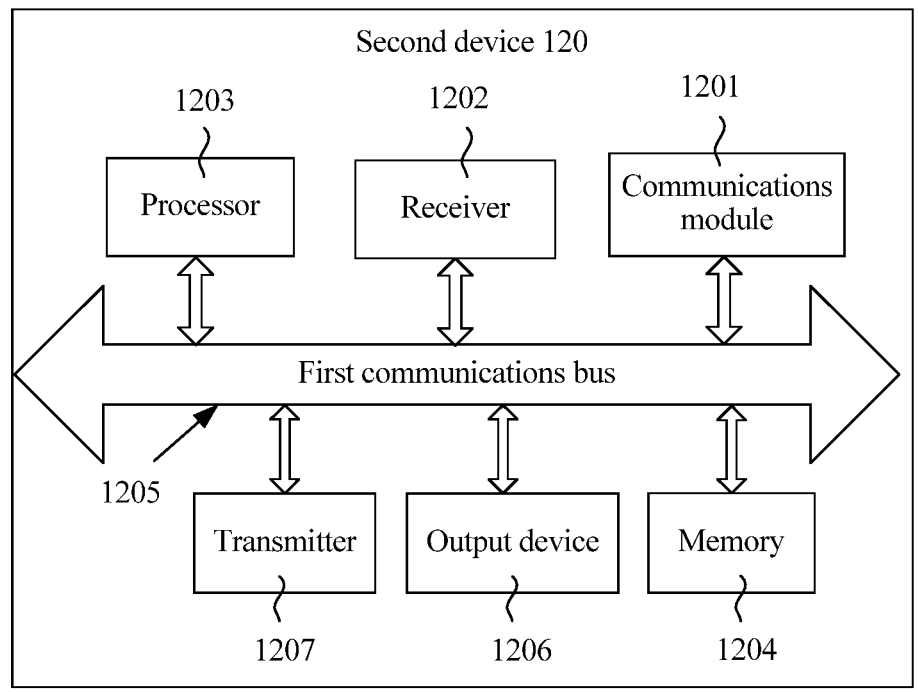
FIG. 13 is a schematic structural diagram of another second device according to an embodiment of the present disclosure.

Optionally, if the execution device is the first device and the presentation device is the second device 120, the receiver 1202 is further configured to receive a presentation instruction message sent by the first device, where the presentation instruction message carries an execution result. As shown in FIG. 13, the second device 120 further includes an output device 1206 configured to present the execution result. The output device 1206 may include but is not limited to a display screen, a speaker, and the like. An output manner of the output device 1206 may include but is not limited to a text, a picture, audio, a video, or the like.

Alternatively, if the execution device is the second device 120 and the presentation device is the first device, as shown in FIG. 13, the second device 120 further includes a transmitter 1207 configured to send an execution result to the first device.

Alternatively, if the second device 120 serves as both the execution device and the presentation device, the receiver 1202 is further configured to receive a presentation instruction message sent by the first device. As shown in FIG. 13, the second device 120 further includes an output device 1206 configured to present an execution result. The output device 1206 may include but is not limited to a display screen, a speaker, and the like. An output manner of the output device 1206 may include but is not limited to a text, a picture, audio, a video, or the like.

Alternatively, if the execution device is the second device 120 and the presentation device is a third device, as shown in FIG. 13, the second device 120 further includes a transmitter 1207 configured to send an execution result to the first device, so that the first device sends a presentation instruction message to the third device, where the presentation instruction message carries the execution result and is used to instruct the third device to present the execution result. The third device is a device, except the second device, that is discovered by the first device and to which the first device establishes a connection. The third device and the first device may be devices carried by a same user, or may be devices carried by different users.

Alternatively, if the execution device is the second device and the presentation device is a third device, the receiver 1202 is further configured to receive a sending instruction message sent by the first device, where the sending instruction message is used to instruct the second device to send an execution result to the third device. As shown in FIG. 13, the second device further includes a transmitter configured to send the execution result to the third device, so that the third device presents the execution result. The third device is a device, except the second device, that is discovered by the first device and to which the first device establishes a connection. The third device and the first device may be devices carried by a same user, or may be devices carried by different users.

Optionally, the receiver 1202 is further configured to receive an instruction message sent by the first device and for stopping execution of the first application; and the processor 1203 is further configured to stop the execution of the first application.

It should be noted that the second device provided in this embodiment can be used to execute the portable device control method shown in the foregoing Embodiment 2. Therefore, for related explanations in this embodiment, reference may be made to Embodiment 2.

The second device provided in this embodiment can execute, under control of a first device, a specific application corresponding to a scene mode. Compared with some approaches in which when a user is in a scene mode, all devices that are carried by the user and can execute a specific application corresponding to the scene mode automatically execute the specific application, the present disclosure reduces total power consumed in a process of executing the specific application.

In the several embodiments provided in the present application, it should be understood that the disclosed device and method may be implemented in other manners. For example, the described device embodiment is merely exemplary. For example, the unit division is merely logical function division and may be other division in some implementations. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electronic or other forms.

The units described as separate parts may or may not be physically separate, and parts displayed as units may or may not be physical units, may be located in one position, or may be distributed on a plurality of network units. Some or all of the units may be selected according to needs to achieve the objectives of the solutions of the embodiments.

In addition, functional units in the embodiments of the present disclosure may be integrated into one processing unit, or each of the units may exist alone physically, or two or more units are integrated into one unit. The integrated unit may be implemented in a form of hardware, or may be implemented in a form of hardware in addition to a software functional unit.

When the foregoing integrated unit is implemented in a form of a software functional unit, the integrated unit may be stored in a computer-readable storage medium. The software functional unit is stored in a storage medium and includes several instructions for instructing a computer device (which may be a personal computer, a server, or a network device) to perform some of the steps of the methods described in the embodiments of the present disclosure. The foregoing storage medium includes any medium that can store program code, such as a USB flash drive, a removable hard disk, a read-only memory (ROM), a RAM, a magnetic disk, or an optical disc.

Finally, it should be noted that the foregoing embodiments are merely intended for describing the technical solutions of the present disclosure but not for limiting the present disclosure. Although the present disclosure is described in detail with reference to the foregoing embodiments, persons of ordinary skill in the art should understand that they may still make modifications to the technical solutions described in the foregoing embodiments or make equivalent replacements to some technical features thereof, without departing from the spirit and scope of the technical solutions of the embodiments of the present disclosure.

What is claimed is:

1. A portable device control method comprising:
    establishing, by a first device using a wireless communications technology, a connection to a second device when the first device discovers the second device;
    determining, by the first device, a user is in a first scene mode, wherein the first scene mode is a sleep status;
    determining, by the first device based on a preset execution policy, an execution device of a first application;
    sending, by the first device to the second device, an instruction message for executing the first application when the execution device is the second device;
    determining, by the first device, that the user is in a second scene mode, wherein the second scene mode is a motion status; and
    sending, by the first device to the second device, an instruction message for stopping the execution of the first application.

2. The method of claim 1, further comprising:
    obtaining, by the first device, an execution result of the first application from the second device when the execution device is the second device; and
    presenting, by the first device, the execution result.

3. The method of claim 1, further comprising sending, by the first device to the second device, a presentation instruction message for presenting an execution result of the first application.

4. The method of claim 1, further comprising sending, by the first device to a third device, a second presentation instruction message, wherein the second presentation instruction message comprises an instruction to the third device to present an execution result of the first application, wherein the third device is discovered by the first device, and wherein the first device establishes another connection to the third device.

5. The method of claim 1, further comprising executing, by the first device, the first application when the execution device is the first device.

6. The method of claim 1, further comprising:
    determining, by the first device, that the user is in a second scene mode, wherein the second scene mode is a motion status; and
    executing, by the first device, the first application.

7. The method of claim 1, wherein before determining that the user is in the first scene mode, the method further comprises obtaining, by the first device, information about a specific application executable by the second device.

8. A portable device control method comprising:
    establishing, by a first device using a wireless communications technology, a connection to a second device when the first device discovers the second device;
    determining, by the first device, a user is in a first scene mode, wherein the first scene mode is a sleep status;
    determining, by the first device based on a preset presentation policy, a presentation device for an execution result of a first application;
    sending, by the first device to the second device, an instruction message for presenting the execution result when the presentation device is the second device;
    determining, by the first device, that the user is in a second scene mode, wherein the second scene mode is a motion status; and
    sending, by the first device to the second device, an instruction message for stopping the presentation of the execution result of the first application.

9. The method of claim 8, further comprising sending, by the first device to a third device, a second presentation instruction message, wherein the second presentation instruction message comprises an instruction to the third device to present the execution result of the first application, wherein the third device is discovered by the first device, and wherein the first device establishes another connection to the third device.

10. The method of claim 8, further comprising:
    determining, by the first device, that the user is in a second scene mode, wherein the second scene mode is a motion status; and
    presenting, by the first device, the execution result of the first application.

11. A first device, comprising:
    a processor configured to:
        discover a second device;
        establish a connection to the second device using a wireless communications technology;

determine that a user is in a first scene mode, wherein the first scene mode is a sleep status; and determine based on a preset execution policy, an execution device of a first application; and a transmitter coupled to the processor, the transmitter configured to:

send an instruction message for executing the first application when the execution device is the second device, wherein the processor is further configured to determine that the user is in a second scene mode, wherein the second scene mode is a motion status, and wherein the transmitter is further configured to send an instruction message for stopping the execution of the first application to the second device.

12. The first device of claim 11, wherein the processor is further configured to:

obtain an execution result of the first application from the second device, when the execution device is the second device; and present the execution result.

13. The first device of claim 11, wherein the transmitter is further configured to send a presentation instruction message for presenting an execution result of the first application to the second device.

14. The first device of claim 11, wherein the transmitter is further configured to send a second presentation instruction message to a third device, wherein the second presentation instruction message comprises an instruction to the third device to present an execution result of the first application, wherein the third device is discovered by the first device, band wherein the first device establishes another connection to the third device.

15. The first device of claim 11, wherein the processor is further configured to execute the first application when the execution device is the first device.

16. The first device of claim 11, wherein the processor is further configured to;

determine that the user is in a second scene mode, wherein the second scene mode is a motion status; and execute the first application.

17. The first device of claim 11, wherein the processor is further configured to obtain information about a specific application executable by the second device.

* * * * *